United States Patent [19]

Hofmann

[11] Patent Number: Plant 5,315

[45] Date of Patent: Oct. 30, 1984

[54] VARIETY OF GERANIUM NAMED 'PALAIS'

[75] Inventor: Guenter Hofmann, Dresden, German Democratic Rep.

[73] Assignee: Oglevee Associates, Inc., Connellsville, Pa.

[21] Appl. No.: 478,145

[22] Filed: Mar. 23, 1983

[51] Int. Cl. ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Robinson & Webb

[57] ABSTRACT

A new geranium cultivar is distinguished by its uniform, salmon color tonality at a distance, more basil branching, more and earlier flowers and big flower heads as compared with commonly grown zonal geraniums.

3 Drawing Figures

BACKGROUND OF THE NEW PLANT

The present invention comprises a new and distinct cultivar of Pelargonium hortorum, Bailey known by the varietal name of Palais. The new variety was discovered in a selective breeding program and is a seedling resulting from the cross of the seed parent (Adonis-×Hannchen Ander)×Rubin selection and the pollen parent Lachsball (pollen mixture).

The new cultivar was discovered in the year 1982 in Dresden, German Democratic Republic; was first asexually reproduced by cuttings in Dresden, German Democratic Republic and has been repeatedly asexually reproduced by cuttings at Oglevee Floral Company in Connellsville, Pa. over an eighteen month period. It has also been trialed and field tested at Connellsville during the summers of 1981 and 1982. It has been found to retain its distinctive characteristics through successive propagation.

The new cultivar, when grown in a greenhouse in Connellsville, Pa., using natural light and 62° F. night temperature and 70° F. day temperature, has a response time of six weeks from a well rooted cutting to a flowering plant in a four inch (10 cm.) pot.

DESCRIPTION OF THE DRAWING

FIG. 1 is a graph of the flavonols fingerprinting.

DESCRIPTION OF THE NEW PLANT

Figure 1:
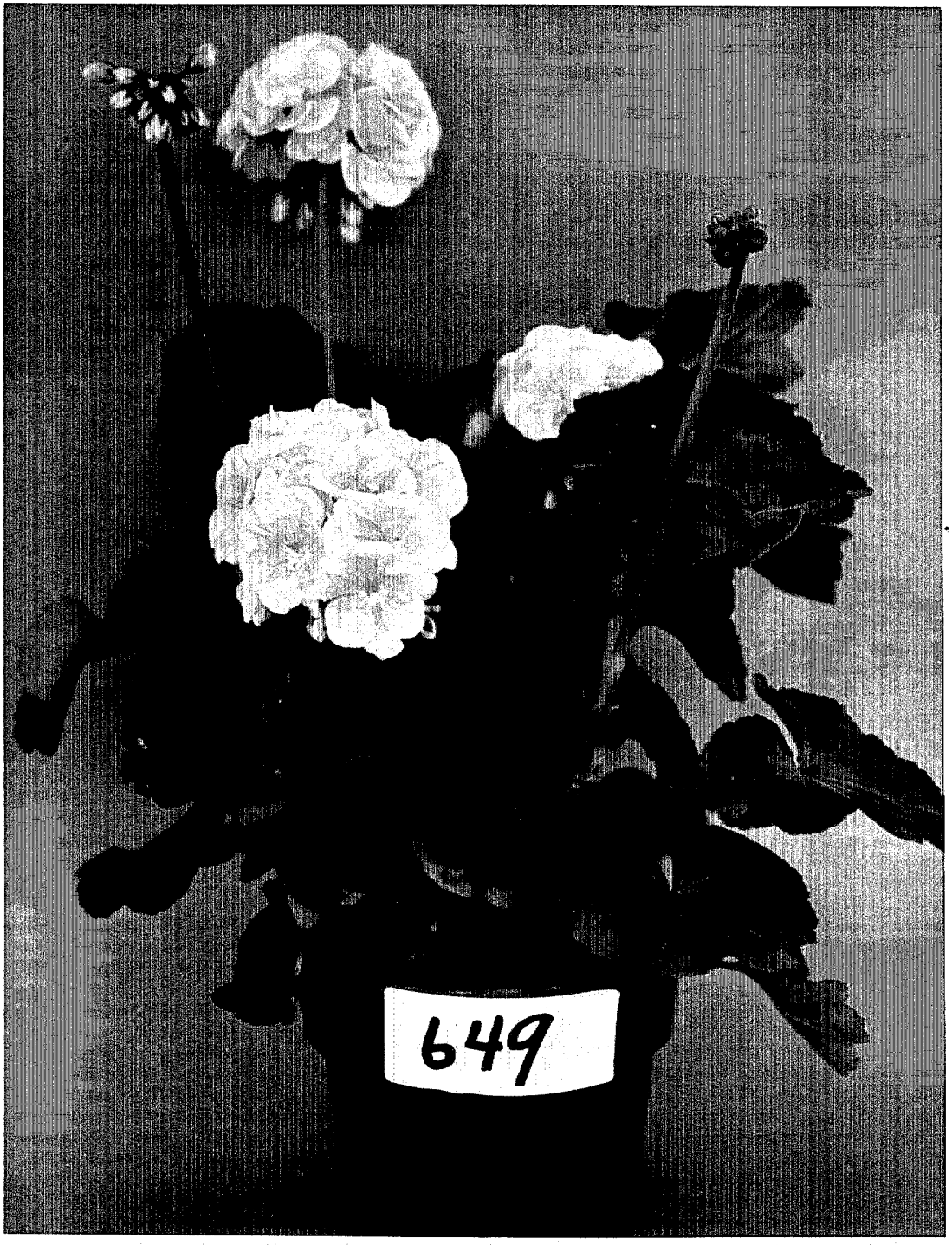
FIG. 1 of the accompanying photographic drawing illustrates the new cultivar, the color being as nearly true as possible with color illustrations of this type.

The following detailed descriptions set forth the characteristics of the new cultivar. The data which define these charcteristics were collected from asexual reproductions carried out by the Oglevee Floral Company in Connellsville, Pa. The plant history was taken on six week plants, blossomed under natural light in a greenhouse and color readings were taken indoors under 100 foot candles of cool, white fluorescent light. Color references are primarily to the R.H.S Colour Chart of The Royal Horticultural Society of London.

THE PLANT

Classification:

*Botannical.*—*Pelargonium hortorum,* Bailey.

*Commercial.*—Zonal geranium.

Form: Bush

Height: 24 to 30 cms. as a four inch pot plant excluding bloom and 30 to 36 cms. as a four inch pot plant including bloom.

Growth: More basil branching and more flower stems as compared with commonly grown zonal geraniums.

Strength: Very sturdy with a low susceptibility to wind and rain damage.

Leaves:

*Size.*—8 To 13 cms. across.

*Shape.*—Reniform with oblique base.

*Margin.*—Cuneate.

*Texture.*—Leathery and pubescent. *Color.*—Upperside—Fan 3 Green Group 137A with inner zone of Fan 3 Green Group 137B. Underside—Fan 3 Green Group 138B.

*Ribs and veins.*—Palmate.

Petioles: 6 to 10 cms.

Stem:

*Color.*—Fan 1 Yellow Green Group 146C.

*Internodes.*—3 To 4 cms.

THE BUD

Shape: Umbel formed with approximately 50 florets.

Size: As bud develops at first color show, head size is 3 to 4 cms. and it opens into a fully developed head size of 10 to 12 cms.

INFLORESCENCE

Blooming Habit: Continuous throughout the year.

Size: 10 To 12 cms. across.

Borne: Singly in an umbel form.

Florets:

*Form.*—Slightly cupped.

*Petals.*—5 To 7 petals, plus 1 to 3 petaloids.

*Upperside.*—Throat area (barely visible) is white. Throat blends into Fan 1 Red Group 38A, which is the predominant color at a distance. Edge area is off-white, Fan 1 Red Group 49B. Pencilling is Fan 1 Red Group 49A and occurs throughout the petal.

*Underside.*—Blend of three colors, namely Fan 1 Red Group 49C, Fan 1 Red Group 49B and Fan 1 Red Group 56C.

*Texture and appearance.*—Firm and satiny.

*Size.*—5 cms.

Petaloids:

*Quantity.*—One to three in number.

*Shape.*—Small and twisted.

*Color.*—Same as florets.

Pedicel:

*Length.*—3 To 3.5 cms.

Peduncle:

*Length.*—17 To 28 cms.

Persistance: Non-shattering.

Disease Resistance: Excellent.

Lasting Quality: Three weeks.

REPRODUCTIVE ORGANS

Stamens:

*Anthers.*—Five to seven, imperfectly formed.

*Filaments.*—Stuck together in cup shape; flattened, white with reddish purple tips, 6 to 8 mms. in length.

*Pollen.*—Reddish brown.

Pistils:

*Number.*—1.

*Length.*—8 To 9 mms.

*Stigma.*—Six arms, reflexed, reddish in color.

*Style.*—Reddish in color.

Ovaries: Green, six carpels.

Fruit: Nonfertile.

The following evaluation is a result of the trialing and field testing carried out in the summer of 1982 at Connellsville, Pa. and compares the new geranium cultivar to a standard cultivar "Wendy Ann" presently commercialized in the United States. The ratings are taken on plants planted in June and evaluated as to height, flowering, number of flowers, heat tolerance and form. The rating is based on a weighted average. A rating of 1.0 is poor and a rating of 10.0 is outstanding.

| CULTIVAR | EVALUATIONS 7/13/82 | 8/15/82 | 9/15/82 | AVERAGE SEASONAL RATING |
|---|---|---|---|---|
| PALAIS | 7.5 | 9.0 | 8.0 | 8.2 |
| WENDY ANN | 8.0 | 7.0 | 7.5 | 7.5 |

The new cultivar is characterized by its uniform salmon color tonality at a distance, more basil branching and width. It is further characterized by more and earlier flowers and bigger flower heads.

Figure 2:
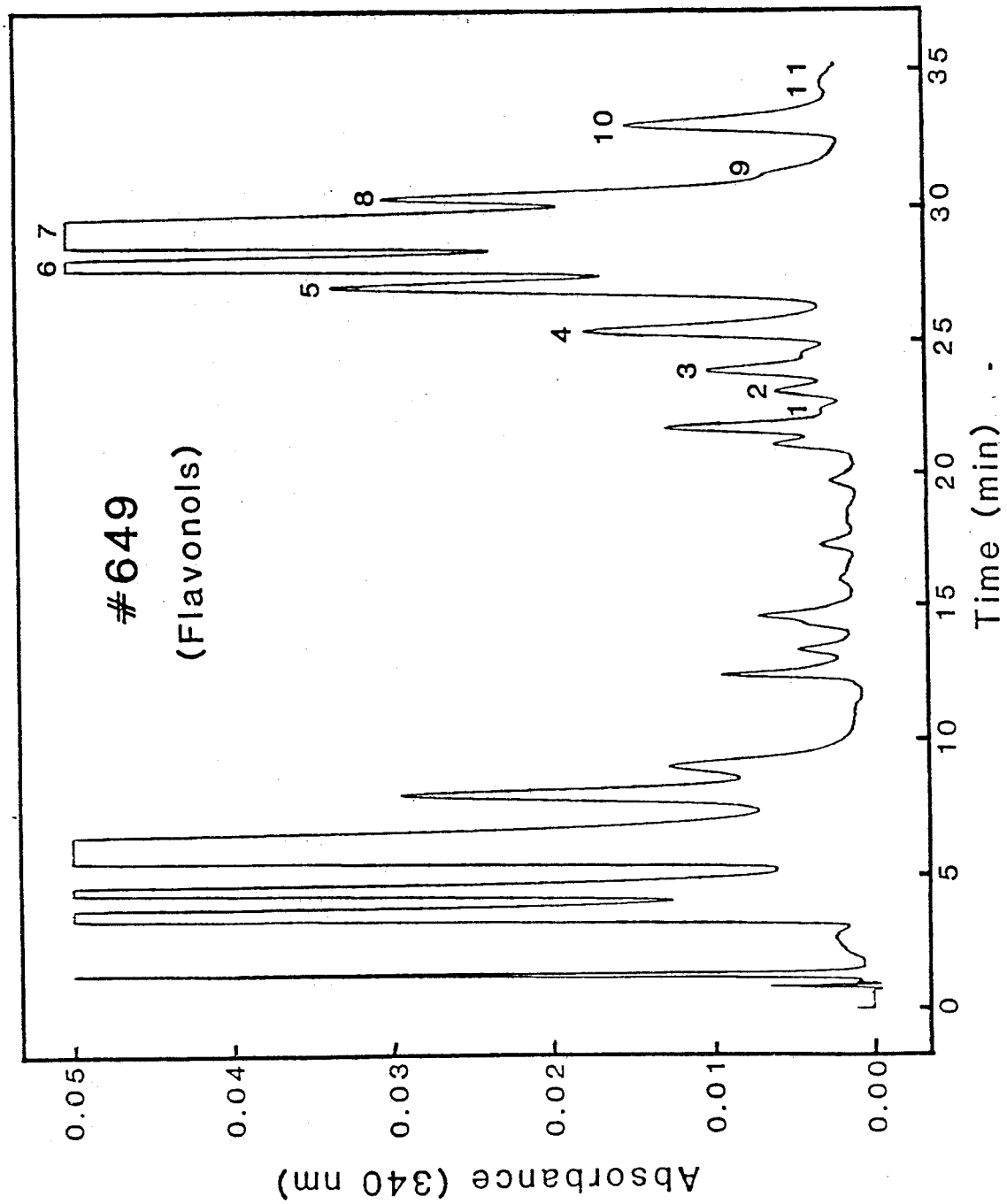
FIG. 2 is a graph of flavonols fingerprinting and FIG. 3 is a graph of the anthocyanins fingerprinting of the new cultivar.
Figure 3:
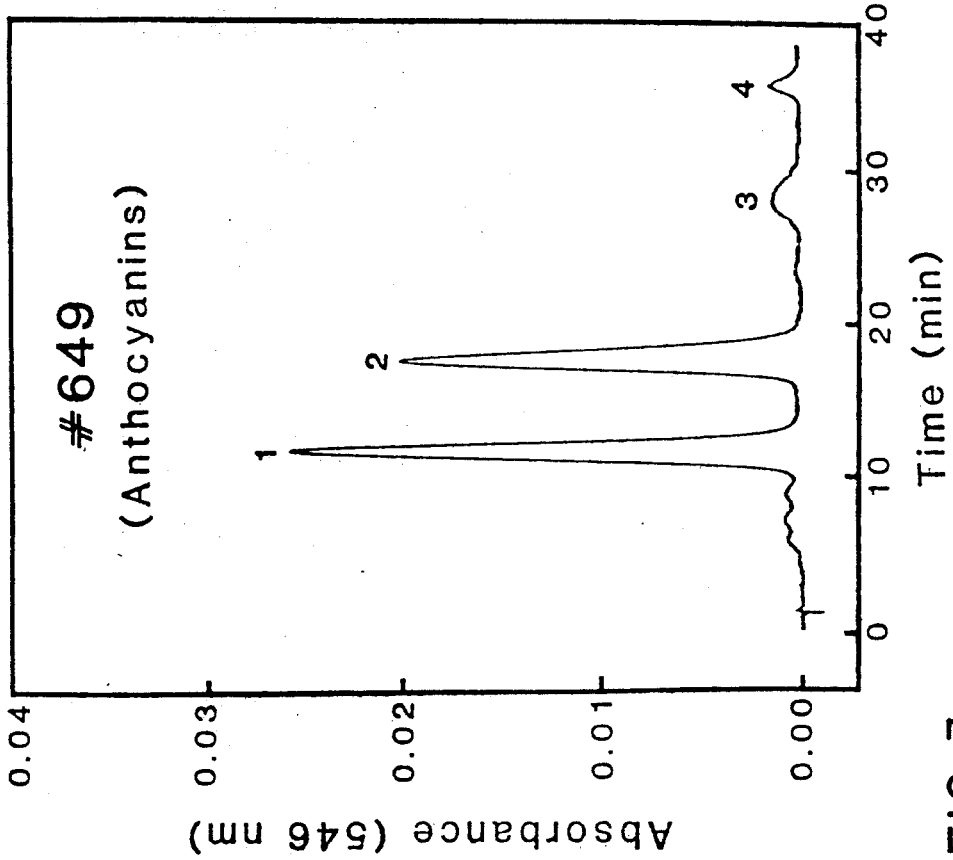

The new cultivar has been fingerprinted by the U.S. Department of Agriculture, Florist and Nursery Crops Laboratory, Beltsville, Md. Young plants arrived from Oglevee Floral Company of Connellsville, Pa. and were grown under standard conditions in a greenhouse at Beltsville, Md. The fingerprinting was conducted by high pressure liquid chromatographic analysis of the anthocyanin and flavonol chemical markers utilizing flower petals as an adjunct for cultivar identification. Petals were selected for analysis from individual mature flowers sampled just after anthesis. It should be noted that changes in environment can influence the biosynthesis of the flavonoids. The absorption profiles (fingerprints) are illustrated in FIGS. 2 and 3.

I claim:

1. A new and distinct variety of geranium plant substantially as herein shown and described.

* * * * *

UNITED STATES PATENT AND TRADEMARK OFFICE

CERTIFICATE OF CORRECTION

PATENT NO. : PP 5,315

DATED : October 30, 1984

INVENTOR(S) : Guenter Hofmann

It is certified that error appears in the above-identified patent and that said Letters Patent is hereby corrected as shown below:

Title page:

IN THE TITLE:

Before "VARIETY" insert --NEW AND DISTINCT--.

Column 1 Line 32 delete

--FIG. 1 is a graph of the flavonols fingerprinting,--.

Signed and Sealed this

*Thirtieth* Day of *April 1985*

[SEAL]

*Attest:*

DONALD J. QUIGG

*Attesting Officer*

*Acting Commissioner of Patents and Trademarks*